United States Patent
Ahmed et al.

(10) Patent No.: US 8,927,560 B2
(45) Date of Patent: Jan. 6, 2015

(54) 4-AZA-2, 3-DIDEHYDROPODOPHYLLOTOXIN COMPOUNDS AND PROCESS FOR THE PREPARATION THEREOF

(75) Inventors: Kamal Ahmed, Hyderabad (IN); Suresh Paidakula, Hyderabad (IN); Ashwini Kumar Banala, Hyderabad (IN); Mallareddy Adla, Hyderabad (IN); Venkat Reddy Papagari, Hyderabad (IN); Rasheed Tamboli Jaki, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 21 days.

(21) Appl. No.: 13/522,219

(22) PCT Filed: Mar. 25, 2011

(86) PCT No.: PCT/IB2011/000641
§ 371 (c)(1),
(2), (4) Date: Jul. 13, 2012

(87) PCT Pub. No.: WO2012/076942
PCT Pub. Date: Jun. 14, 2012

(65) Prior Publication Data
US 2013/0245048 A1    Sep. 19, 2013

(30) Foreign Application Priority Data
Dec. 6, 2010   (IN) .......................... 2887/DEL/2010

(51) Int. Cl.
| | | |
|---|---|---|
| A61K 31/505 | (2006.01) |
| A01N 43/54 | (2006.01) |
| A01N 43/42 | (2006.01) |
| A61K 31/44 | (2006.01) |
| C07D 491/00 | (2006.01) |
| C07D 239/00 | (2006.01) |
| C07D 471/00 | (2006.01) |
| C07D 487/00 | (2006.01) |
| C07D 261/20 | (2006.01) |
| C07D 498/00 | (2006.01) |
| C07D 491/04 | (2006.01) |
| C07D 498/14 | (2006.01) |
| C07D 498/04 | (2006.01) |
| C07D 491/147 | (2006.01) |
| C07D 513/04 | (2006.01) |

(52) U.S. Cl.
CPC ............ C07D 498/14 (2013.01); C07D 491/04 (2013.01); C07D 498/04 (2013.01); C07D 491/147 (2013.01); C07D 513/04 (2013.01)
USPC ............ 514/267; 514/292; 544/250; 548/242

(58) Field of Classification Search
CPC ............. A61K 31/519; A61K 31/4355; C07D 273/01; C07D 491/147
USPC .................... 514/267, 292; 544/250; 548/242
See application file for complete search history.

(56) References Cited

U.S. PATENT DOCUMENTS

| | | |
|---|---|---|
| 6,548,515 B1 | 4/2003 | Husson et al. |
| 2004/0198981 A1 | 10/2004 | Husson et al. |

OTHER PUBLICATIONS

Kamal et. al., Bioorganic and Medicinal Chemistry, 2011, Elsevier, vol. 19, pp. 2349-2358.*
International Search Report of PCT/IB2011/000641, Jun. 30, 2011.

* cited by examiner

*Primary Examiner* — Sarah Pihonak
(74) *Attorney, Agent, or Firm* — Edwards Wildman Palmer LLP; Jeffrey D. Hsi

(57) ABSTRACT

The present invention provides 4-Aza-2,3-didehydropodophyllotoxin compound of general formula A (4a-4z and 4aa-4ae) as useful potential antitumour agents against human cancer cell lines. The present invention further provides a process for the synthesis of 4-Aza-2,3-didehydropodophyllotoxin compounds (4a-4z and 4aa-4ae).

Formula A

15 Claims, No Drawings

4-AZA-2, 3-DIDEHYDROPODOPHYLLOTOXIN COMPOUNDS AND PROCESS FOR THE PREPARATION THEREOF

CROSS REFERENCE TO RELATED APPLICATIONS

This application is the national phase under 35 U.S.C. §371 of PCT International Application No. PCT/IB2011/000641, filed Mar. 25, 2011, which claims the benefit of Indian Patent Application No. 2887/DEL/2010, filed Dec. 6, 2010, the entire contents of the aforementioned applications are hereby incorporated herein by reference.

FIELD OF THE INVENTION

The present invention relates to 4-Aza-2,3-didehydropodophyllotoxin compounds as antitumour agents. More particularly, the present invention provides a process for the preparation of 4-Aza-2,3-didehydropodophyllotoxin compounds. The structural formulas of these new 4-Aza-2,3-didehydropodophyllotoxin compounds are given below.

BACKGROUND OF THE INVENTION

Etoposide and teniposide are semisynthetic podophyllotoxin derivatives that are in clinical usage as anticancer drugs FIG. 1 (Chen. Y. Z.; Wang. Y. G.; Tian, X.; Li, J. X. *Curr. Sci* 1990, 59, 517; Wang, J. Z.; Tian, X.; Tsumura, H.; Shimura, K.; Ito, H. *Anti-cancer Drug Design,* 1993, 8, 193).

It is believed that analogues of 4'-demethyl epipodophyllotoxin exert their antitumour activity through stabilization of a cleavable complex between DNA and type-II DNA topoisomerase, this leads ultimately to inhibition of DNA catenation activity and produces single and double strand breaks (Satio, H.; Yoshikawa, H.; Nishimura, Y.; Kondo, S.; Takeuchi, T.; Umezawa, H. *Chem Pharm. Bull.* 1986, 34, 3733; Chen, Y. Z.; Wang, Y. G.; Li, J. X.; Tian, X.; Jia. Z. P.; Zhang, Z. Y. *Life Sci.* 1989, 45, 2569).

A number of studies have been carried out on the structural modification of glycoside by amino substituents that has improved the inhibitory activity on human DNA topoisomerase-II as well as stronger activity in causing cellular protein length DNA breakage (Lee, K. H.; Imakura, Y.; Haruna, M.; Beers, S. A.; Thurston, L. S.; Dai, H. J.; Chen, C. H.; Liu, S. Y.; Cheng, Y. C. *J. Nat. Prod.* 1989, 52, 606; Liu, S. Y.; Hawang, B. D.; Haruna, M.; Imakura, Y.; Lee, K. H.; Cheng, Y. C. *Mol. Pharmacol.* 1989, 36, 8; Lee, K, H.; Beers, S. A.; Mori, M.; Wang, Z. Q.; Kuo, Y. H.; Li, L.; Liu, S. Y.; Cheng, Y. C.; *J. Med. Chem.* 1990, 33, 1364; Kamal, A.; Gayatri, N. L.; Reddy, D. R.; Reddy, P, S. M. M.; Arifuddin, M.; Dastidar, S. G.; Kondapi, M. A.; Rajkumar M. *Bioorg. Med. Chem.* 2005, 13, 6218; Kamal, A.; Kumar, B. A.; Arifuddin, M.; Dastidar, S. G. *Bioorg. Med. Chem.* 2003, 11, 5135).

A number of studies have been carried out on the structural modification of podophyllotoxin. Itokawa and Takeya made an important contribution to the field by demonstrating that greatly simplified 4-Aza-2,3-didehydropodophyllotoxins retain a most of the cytotoxicity associated with the parent lignan (Hitotsuyanagi, Y.; Kobayashi, M.; Fukuyo, M.; Takeya, K.; Itokawa, H.

A facile synthesis of the 4-Aza-analogs of 1-arylnaphthalene lignans —Chinensin, justicidin B, and Taiwanin C. *Tetrahedron Lett.* 1997, 38, 8295-8296; Hitotsuyanagi, Y.; Fukuyo, M.; Tsuda, K.; Kobayashi, M.; Ozeki, A.; Itokawa, H.; Takeya, K. 4-Aza-2,3-dehydro-4-deoxypodophyllotoxins: Simple Aza-podophyllotoxin analogues possessing potent cytotoxicity. *Bioorg. Med. Chem. Lett.* 2000, 10, 315-317). In this context a large number of 4-Aza-2,3-didehydro podophyllotoxins derivatives have been synthesized and investigated for their antitumour activity.

FIG. -1

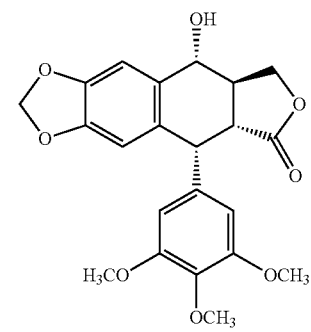

Podophyllotoxin

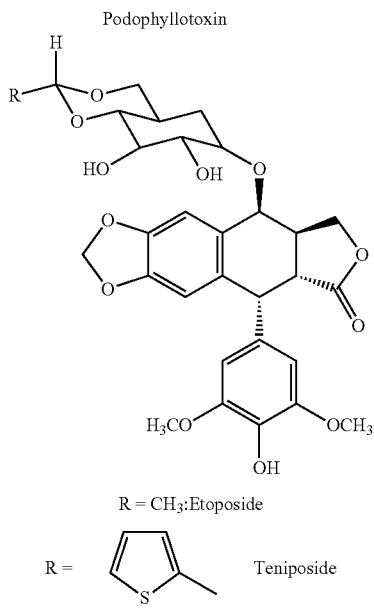

R = CH$_3$:Etoposide

R = [thiophene] Teniposide

OBJECT OF THE INVENTION

The main object of the invention is to provide the new 4-Aza-2,3-didehydropodophyllotoxin compounds as useful antitumour agents.

Another object of the present invention is to provide a process for the synthesis of these new 4-Aza-2,3-didehydro derivatives of podophyllotoxin as useful anticancer agents.

Yet another object of the present invention is to provide new compounds based on the podophyllotoxin in good yields.

SUMMARY OF THE INVENTION

The present invention provides compound of general formula A (4a-4z and 4aa-4ae) as useful potential antitumour agents against human cancer cell lines. The present invention further provides a process for the synthesis of new 4-Aza-2, 3-didehydropodophyllotoxin compounds (4a-4z and 4aa-4ae).

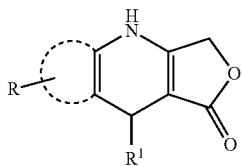

Formula A

Wherein, R is selected from 2,4 dimethoxy 5-pyrimidyl, 5-indyl, 2-methyl-5-indyl, 5-indazolyl, 6-benthiazolyl, 2-methyl-6-benthiazolyl, 2-mercapto-5-imidazolyl, 5-triazolyl, 3-(4-methoxyphenyl) 5-isoxazolyl, 3-(4-chlorophenyl) 5-isoxazolyl, 2,3,4,-trimethoxyphenyl and $R^1$ is selected from 3,4,5-trimethoxyphenyl, 4-hydroxy-3-methoxyphenyl, 3-hydroxy-4-methoxyphenyl, 4-fluoro-3-methoxyphenyl, 3-nitro-4-methoxyphenyl, 2-fluoro-4-methoxyphenyl.

DESCRIPTION OF THE INVENTION

Accordingly, the present invention relates to 4-Aza-2,3-didehydropodophyllotoxin compounds as antitumour agents. More particularly, the present invention provides a process for the preparation of 4-Aza-2,3-didehydropodophyllotoxin compounds having the structural formula as follows

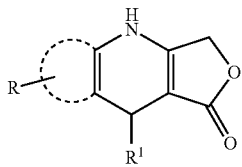

Formula A

In one embodiment of the present invention, 4-Aza-2,3-didehydropodophyllotoxin compound is represented by the group of the following compounds:
2,4-dimethoxy-5-(3,4,5-trimethoxyphenyl)-5,6,8,9-tetrahydrofuro[3',4':5,6]pyrido[2,3-d]pyrimidin-6-one (4a);
5-(4-hydroxy-3-methoxyphenyl)-2,4-dimethoxy-5,6,8,9-tetrahydrofuro[3',4':5,6]pyrido[2,3-d]pyrimidin-6-one (4b);
5-(3-hydroxy-4-methoxyphenyl)-2,4-dimethoxy-5,6,8,9-tetrahydrofuro[3',4':5,6]pyrido[2,3-d]pyrimidin-6-one (4c);
5-(4-fluoro-3-methoxyphenyl)-2,4-dimethoxy-5,6,8,9-tetrahydrofuro[3',4':5,6]pyrido[2,3-d]pyrimidin-6-one (4d);
10-(3,4,5-trimethoxyphenyl)-6,7,9,10-tetrahydro-1H-furo[3,4-b]pyrrolo[2,3-f]quinolin-9-one (4e);
10-(4-hydroxy-3-methoxyphenyl)-6,7,9,10-tetrahydro-1H-furo[3,4-b]pyrrolo[2,3-f]quinolin-9-one (4f);
10-(3-hydroxy-4-methoxyphenyl)-6,7,9,10-tetrahydro-1H-furo[3,4-b]pyrrolo[2,3-f]quinolin-9-one (4g);
10-(4-fluoro-3-methoxyphenyl)-6,7,9,10-tetrahydro-1H-furo[3,4-b]pyrrolo[2,3-f]quinolin-9-one (4h);
10-(4-methoxy-3-nitrophenyl)-6,7,9,10-tetrahydro-1H-furo[3,4-b]pyrrolo[2,3-f]quinolin-9-one (4i);
2-methyl-10-(3,4,5-trimethoxyphenyl)-6,7,9,10-tetrahydro-1H-furo[3,4-b]pyrrolo[2,3-f]quinolin-9-one (4j);
10-(3-hydroxy-4-methoxyphenyl)-2-methyl-6,7,9,10-tetrahydro-1H-furo[3,4-b]pyrrolo[2,3-f]quinolin-9-one (4k);
10-(4-fluoro-3-methoxyphenyl)-2-methyl-6,7,9,10-tetrahydro-1H-furo[3,4-b]pyrrolo[2,3-f]quinolin-9-one (4l);
10-(2-fluoro-4-methoxyphenyl)-2-methyl-6,7,9,10-tetrahydro-1H-furo[3,4-b]pyrrolo[2,3-f]quinolin-9-one (4m);
10-(3,4,5-trimethoxyphenyl)-6,7,9,10-tetrahydro-1H-furo[3,4-b]pyrazolo[3,4-f]quinolin-9-one (4n);
10-(4-hydroxy-3-methoxyphenyl)-6,7,9,10-tetrahydro-1H-furo[3,4-b]pyrazolo[3,4-f]quinolin-9-one (4o);
10-(3-hydroxy-4-methoxyphenyl)-6,7,9,10-tetrahydro-1H-furo[3,4-b]pyrazolo[3,4-f]quinolin-9-one (4p);
10-(4-fluoro-3-methoxyphenyl)-6,7,9,10-tetrahydro-1H-furo[3,4-b]pyrazolo[3,4-f]quinolin-9-one (4q);
10-(4-methoxy-3-nitrophenyl)-6,7,9,10-tetrahydro-1H-furo[3,4-b]pyrazolo[3,4-f]quinolin-9-one (4r);
10-(3,4,5-trimethoxyphenyl)-6,7,9,10-tetrahydrofuro[3,4-b][1,3]thiazolo[5,4-f]quinolin-9-one (4s);
10-(4-hydroxy-3-methoxyphenyl)-6,7,9,10-tetrahydrofuro[3,4-b][1,3]thiazolo[5,4-f]quinolin-9-one (4t);
10-(3-hydroxy-4-methoxyphenyl)-6,7,9,10-tetrahydrofuro[3,4-b][1,3]thiazolo[5,4-f]quinolin-9-one (4u);
10-(4-hydroxy-3-methoxyphenyl)-2-methyl-6,7,9,10-tetrahydrofuro[3,4-b][1,3]thiazolo[5,4-f]quinolin-9-one (4v);
10-(3-methoxy-4-nitrophenyl)-2-methyl-6,7,9,10-tetrahydrofuro[3,4-b][1,3]thiazolo[5,4-f]quinolin-9-one (4w);
10-(3-hydroxy-4-methoxyphenyl)-2-sulfanyl-6,7,9,10-tetrahydro-1H-furo[3,4-b]imidazo[4,5-f]quinolin-9-one (4x);
10-(3,4,5-trimethoxyphenyl)-6,7,9,10-tetrahydro-1H-furo[3,4-b][1,2,3]triazolo[4,5-f]quinolin-9-one (4y);
10-(2-fluoro-4-methoxyphenyl)-6,7,9,10-tetrahydro-1H-furo[3,4-b][1,2,3]triazolo[4,5-f]quinolin-9-one (4z);
3-(4-methoxyphenyl)-4-(3,4,5-trimethoxyphenyl)-4,5,7,8 tetrahydrofuro[3',4':5,6]pyrido[3,2-d]isoxazol-5-one (4aa);
4-(3-hydroxy-4-methoxyphenyl)-3-(4-methoxyphenyl)-4,5,7,8-tetrahydrofuro[3',4':5,6]pyrido[3,2-d]isoxazol-5-one (4ab);
3-(4-chlorophenyl)-4-(3,4,5-trimethoxyphenyl)-4,5,7,8-tetrahydrofuro[3',4':5,6]pyrido[3,2-d]isoxazol-5-one (4ac);
3-(4-chlorophenyl)-4-(3-hydroxy-4-methoxyphenyl)-4,5,7,8-tetrahydrofuro[3',4':5,6]pyrido[3,2-d]isoxazol-5-one (4ad);
9-(4-hydroxy-3-methoxyphenyl)-5,6,7-trimethoxy-1,3,4,9-tetrahydrofuro[3,4-b]quinolin-1-one (4ae);

In another embodiment of the present invention, 4-Aza-2, 3-didehydropodophyllotoxin compounds as claimed, wherein the structural formulae of the representative compounds are:

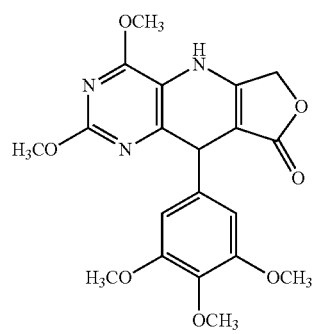

4a

4b 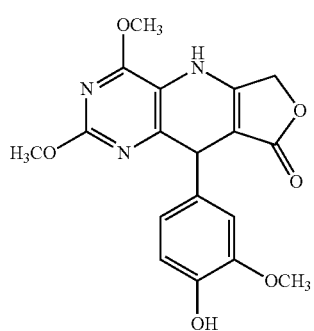
4c 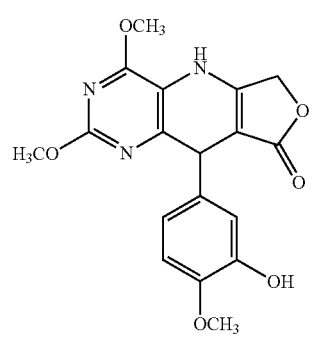
4d 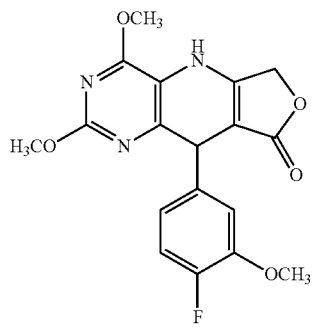
4e 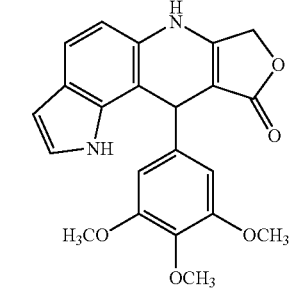
4f 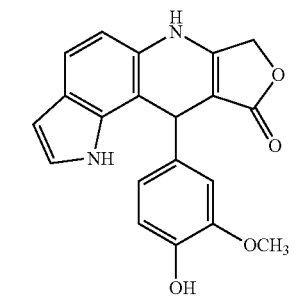
4g 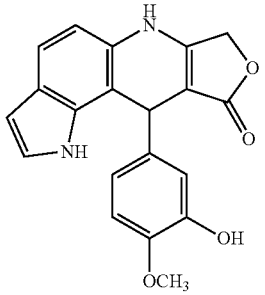
4h 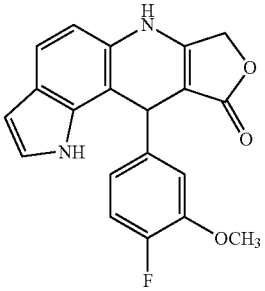
4i 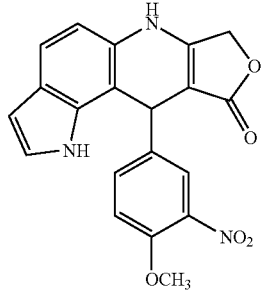
4j 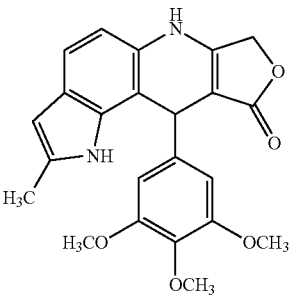
4k 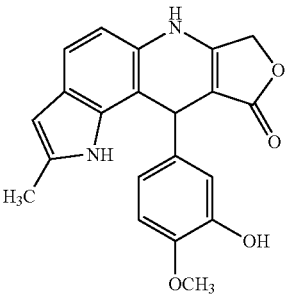

-continued
4l
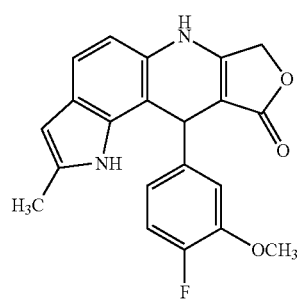
4m
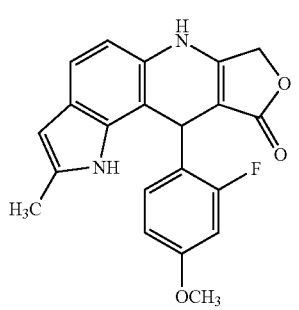
4n
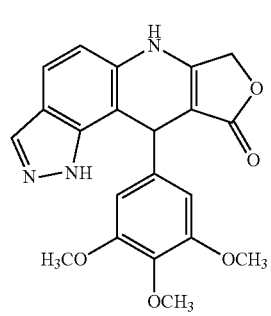
4o
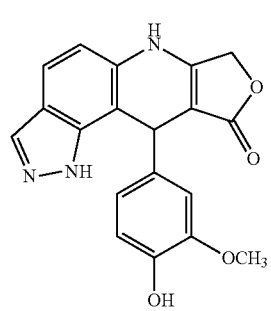
4p
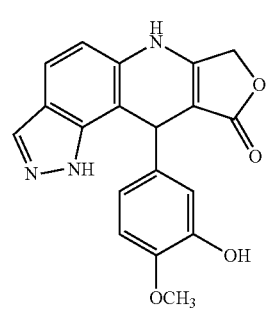
-continued
4q
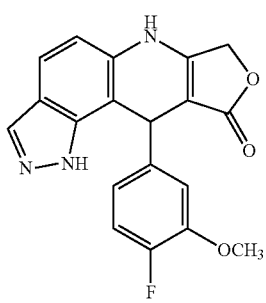
4r
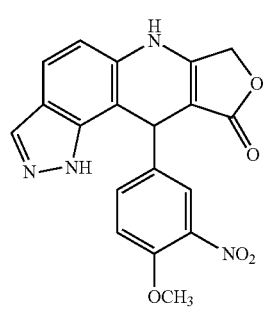
4s
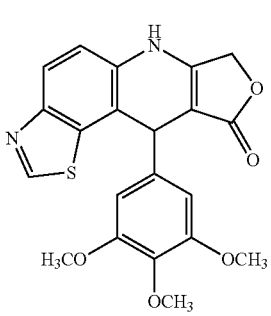
4t
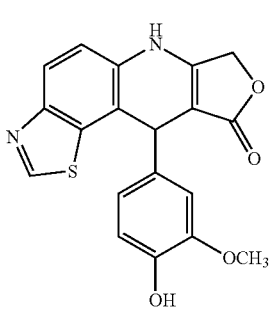
4u
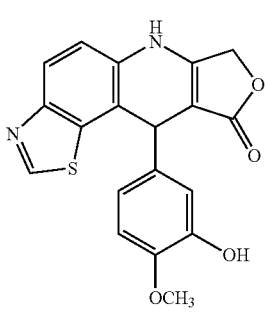

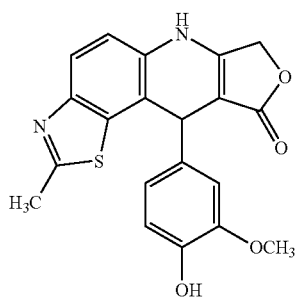 4v
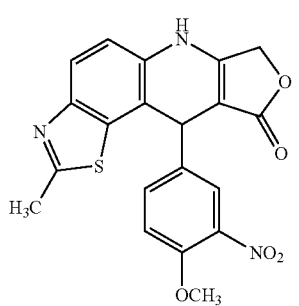 4w
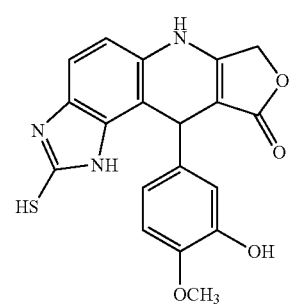 4x
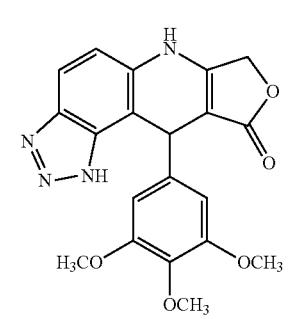 4y
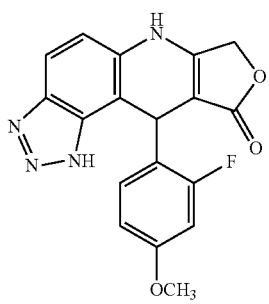 4z
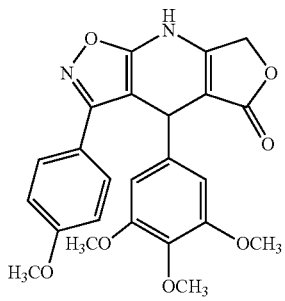 4aa
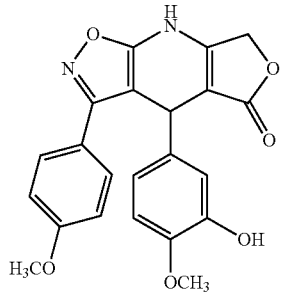 4ab
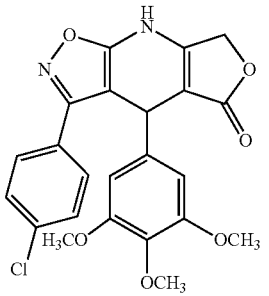 4ac
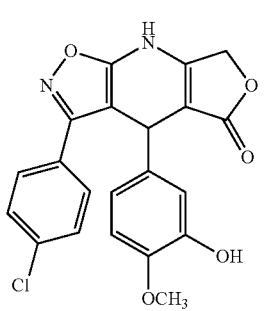 4ad

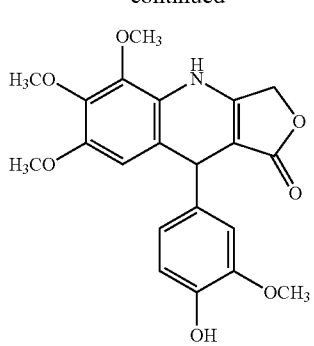

4ae

In another embodiment of the present invention, 4-Aza-2, 3-didehydropodophyllotoxin compounds exhibiting in vitro anticancer activity against human cancer cell lines selected from the group consisting of colon (Colo205), lung (Hop-62, A549), cervix (SiHa), prostate (PC3), oral (KB, DWD, Gurav), Ovarian (A-2780) and breast (MCF7, Zr-75-1).

In another embodiment of the present invention, 4-Aza-2, 3-didehydropodophyllotoxin compounds 4a-4z and 4aa-4ae as claimed, wherein the concentration of the compound used for in vitro activity against breast cancer cell lines for $GI_{50}$ is in the range of 0.1 to 2.9 μm at an exposure period of at least 48 hrs.

In another embodiment of the present invention, 4-Aza-2, 3-didehydropodophyllotoxin compounds 4a-4z and 4aa-4ae as claimed, wherein the concentration of the compound used for in vitro activity against oral cancer cell lines for $GI_{50}$ is in the range of 0.12 to 2.9 μm at an exposure period of at least 48 hrs.

In another embodiment of the present invention, 4-Aza-2, 3-didehydropodophyllotoxin compounds 4a-4z and 4aa-4ae, wherein the concentration of the compound used for in vitro activity against colon cancer cell lines for $GI_{50}$ is in the range of 0.15 to 2.7 μm at an exposure period of at least 48 hrs.

In another embodiment of the present invention, 4-Aza-2, 3-didehydropodophyllotoxin compounds 4a-4z and 4aa-4ae as claimed, wherein the concentration of the compound used for in vitro activity against lung cancer cell lines for $GI_{50}$ is in the range of 0.1 to 2.8 μm at an exposure period of at least 48 hrs.

In another embodiment of the present invention, 4-Aza-2, 3-didehydropodophyllotoxin compounds 4a-4z and 4aa-4ae as claimed, wherein the concentration of the compound used for in vitro activity against prostate cancer cell lines for $GI_{50}$ is in the range of 0.16 to 2.4 μm at an exposure period of at least 48 hrs.

In another embodiment of the present invention, 4-Aza-2, 3-didehydropodophyllotoxin compounds 4a-4z and 4aa-4ae as claimed, wherein the concentration of the compound used for in vitro activity against cervix cancer cell lines for $GI_{50}$ is in the range of 0.18 to 2.6 μm at an exposure period of at least 48 hrs.

In another embodiment of the present invention, 4-Aza-2, 3-didehydropodophyllotoxin compounds 4a-4z and 4aa-4ae as claimed, wherein the concentration of the compound used for in vitro activity against ovarian cancer cell lines for $GI_{50}$ is in the range of 0.12 to 2.7 μm at an exposure period of at least 48 hrs.

In another embodiment of the present invention, a pharmaceutical composition comprising compound of formula, or pharmaceutically acceptable salts, excipients and carriers thereof.

In another embodiment of the present invention, a process for the preparation of 4-Aza-2,3-didehydropodophyllotoxin compounds of Formula A.

Formula A

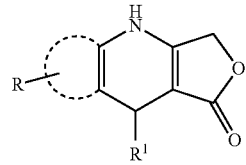

(a) refluxing substituted heteroaromatic amines, tetronic acid, and a corresponding substituted aromatic aldehydes in an organic solvent at temperature ranging between 70-78° C. for a period ranging between 60-90 min;

(b) cooling the reaction mixture as obtained in step (a) at temperature ranging between 25-35° C.;

(c) filtering the reaction mixture as obtained in step (b) at vacuum to obtain crude product followed by washing the crude product with an organic solvent;

(d) recrystallizing the crude as obtained in step (c) in an organic solvent to obtain pure 4-Aza-2,3-didehydropodophyllotoxin compounds of formula A.

In another embodiment of the present invention, a process as claimed, wherein mol ratio of heteroaromatic amines, tetronic acid, and aromatic aldehydes used is 1:1:1.

In another embodiment of the present invention, a process as claimed, wherein an organic solvent used in process is selected from the group of methanol, ethanol and DMF.

Thus the present invention provides new class of 4-Aza-2, 3-didehydropodophyllotoxin compounds. A synthesis of new substituted 4-Aza-didehydropodophyllotoxin compounds with enhanced anticancer activity and/or activity against etoposide resistant tumor cell lines. In these efforts new 4-Aza-2,3-didehydropodophyllotoxin derivatives have been synthesized and evaluated for their cytotoxicity and anticancer potency compared to adiramycin. The synthesis of these compounds has been carried out as described in the Scheme I using substituted aromatic aldehydes, substituted heteroaromatic amines and tetronic acid.

Scheme 1

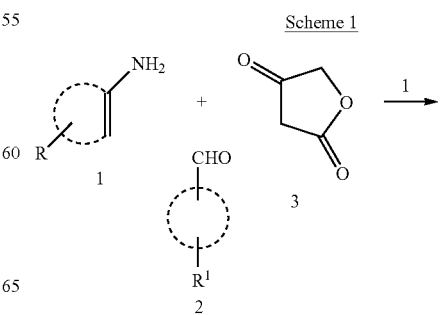

-continued

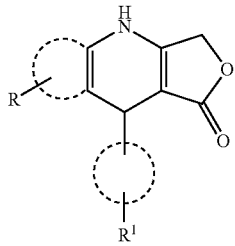

4a-4z and 4aa-4ae

R = 2,4 dimethoxy 5-pyrimidyl, R$^1$ = 3,4,5-trimethoxyphenyl
R = 2,4 dimethoxy 5-pyrimidyl, R$^1$ = 4-hydroxy-3-methoxphenyl
R = 2,4 dimethoxy 5-pyrimidyl, R$^1$ = 3-hydroxy-4-methoxyphenyl
R = 2.4 dimethoxy 5-pyrimidyl, R$^1$ = 4-fluoro-3-methoxyphenyl
R = 5-indyl, R$^1$ = 3,4,5-trimethoxyphenyl
R = 5-indyl, R$^1$ = 4-hydroxy-3-methoxyphenyl
R = 5-indyl, R$^1$ = 3-hydroxy-4-methoxyphenyl
R = 5-indyl, R$^1$ = 4-fluoro-3-methoxyphenyl
R = 5-indyl, R$^1$ = 3-nitro-4-methoxyphenyl
R = 2-methyl-5-indyl, R$^1$ = 3,4,5-trimethoxyphenyl
R = 2-methyl-5-indyl, R$^1$ = 3-hydroxy-4-methoxyphenyl
R = 2-methyl-5-indyl, R$^1$ = 4-fluoro-3-methoxyphenyl
R = 2-methyl-5-indyl, R$^1$ = 2-fluoro-4-methoxyphenyl
R = 5-indazolyl, R$^1$ = 3,4,5-trimethoxyphenyl
R = 5-indazolyl, R$^1$ = 4-hydroxy-3-methoxyphenyl
R = 5-indazoly, R$^1$ = 3-hydroxy-4-methoxyphenyl
R = 5-indazolyl, R$^1$ = 4-fuoro-3-methoxyphenyl
R = 5-indazolyl, R$^1$ = 3-nitro-4-methoxyphenyl
R = 6-benzthiazolyl, R$^1$ = 3,4,5-trimethoxyphenyl
R = 6-benzthiazolyl, R$^1$ = 4-hydroxy-3-methoxyphenyl
R = 6-benzthiazolyl, R$^1$ = 3-hydroxy-4-methoxyphenyl
R = 2-methyl-6-benzthiazolyl, R$^1$ = 4-hydroxy-3-methoxyphenyl
R = 2-methyl-6-benzthiazolyl, R$^1$ = 3-nitro-4-methoxyphenyl
R = 2-mercapto-5-imidazolyl, R$^1$ = 3-hydroxy-4-methoxyphenyl
R = 5-triazolyl, R$^1$ = 3,4,5-trimethoxypheny
R = 5-triazolyl, R$^1$ = 2-fluoro-4-methoxyphenyl
R = 3-(4-methoxyphenyl)5-isoxazolyl, R$^1$ = 3,4,5-trimethoxyphenyl
R = 3-(4-methoxyphenyl)5-isoxazolyl, R$^1$ = 3-hydroxy-4-methoxyphenyl
R = 3-(4-chlorophenyl)5-isoxazolyl, R$^1$ = 3,4,5-trimethoxyphenyl
R = 3-(4-chlorophenyl)5-isoxazolyl, R$^1$ = 3-hydroxy-4-methoxyphenyl
R = 2,3,4-trimethoxyphenyl, R$^1$ = 4-hydroxy-3-methoxyphenyl;

The following examples are given by way of illustration and therefore should not be construed to the present limit of the scope of invention.

General Procedure for Synthesis

General procedure for 4-Aza-2,3-didehydropodophyllotoxin Synthesis (1). A mixture of substituted heteroaromatic amines (1 eq), tetronic acid (1 eq), and a corresponding substituted aromatic aldehydes (1 eq) in EtOH (4 mL) was refluxed at temperature 78° C. for 1 h. The reaction mixture was allowed to cool to room temperature 25° C., and the precipitated product was collected by vacuum filtration and washed with EtOH (3 mL) at room temperature 25° C. and then recrystallized with ethanol (15 mL and 78° C.) to give pure compounds in 90-98% yield in all case.

Example 1

2,4-dimethoxy-5-(3,4,5-trimethoxyphenyl)-5,6,8,9 tetrahydrofuro[3',4':5,6]pyrido[2,3-d]pyrimidin-6-one (4a)

This compound was prepared by method described above employing 3,4,5-trimethoxybenzaldehyde (200 mg, 1.020 mmol), tetronic acid (102 mg, 1.020 mmol) and 2,4-dimethoxypyrimidine-5-amine (158 mg, 1.020 mmol) to affords 4a, 390 mg in 92% yield. Mp: 299-300° C., $^1$H NMR (200 MHz, DMSO-d$_6$): δ 3.61 (s, 3H), 3.70 (s, 6H), 3.81 (s, 3H), 3.85 (s, 3H), 4.79-5.02 (m, 3H), 6.43 (s, 2H), 10.61 (s, 1H); $^{13}$C NMR (75 MHz, DMSO-d$_6$): δ 34.3, 53.8, 54.3, 55.7, 59.7, 65.2, 93.8, 99.6, 104.7, 136.1, 139.9, 152.4, 156.8, 163.2, 168.8, 171.1; MS (ESI): 416 [M$^+$+H]; HRMS (ESI) calcd for C$_{20}$H$_{22}$N$_3$O$_7$ ([M+Na]$^+$) 416.1457. found: 416.1447.

Example 2

5-(4-hydroxy-3-methoxyphenyl)-2,4-dimethoxy-5,6,8,9tetrahydrofuro[3',4':5,6]pyrido[2,3-d]pyrimidin-6-one (4b)

This compound was prepared by method described above employing 4-hydroxy-3-methoxybenzaldehyde (200 mg, 1.273 mmol) tetronic acid (127 mg, 1.273 mmol) and 2,4-dimethoxypyrimidine-5-amine (197 mg, 1.273 mmol) to affords 4b, 450 mg in 92% yield. Mp: 294-296° C., $^1$H NMR (200 MHz, DMSO-d$_6$): δ3.77 (s, 3H), 3.84 (s, 3H), 3.90 (s, 3H), 4.82-5.03 (dd, 2H, J=16.8, 16.8 Hz), 6.47-6.52 (dd, 1H, J=2.1, 2.1 Hz), 6.66 (l, 1H, J=8.0 Hz), 6.84 (d, 1H, J=2.1 Hz), 10.64 (s, 1H); $^{13}$C NMR (75 MHz, DMSO-d$_6$): δ 33.5, 53.8, 54.2, 55.4, 65.1, 94.3, 100.2, 111.8, 115.1, 119.4, 135.6, 145.0, 146.9, 156.6, 157.5, 163.0, 168.7, 171.1; MS (ESI): 372 [M$^+$+H]; HRMS (ESI) calcd for C$_{20}$H$_{16}$N$_2$O$_4$Na ([M+Na]$^+$) 371.1007. found: 371.0995.

Example 3

5-(3-hydroxy-4-methoxyphenyl)-2,4-dimethoxy-5,6,8,9-tetrahydrofuro[3',4':5,6]pyrido[2,3-d]pyrimidin-6-one (4c)

This compound was prepared by method described above employing 3-hydroxy-4-methoxybenzaldehyde (200 mg, 1.273 mmol) tetronic acid (127 mg, 1.273 mmol) and 2,4-dimethoxypyrimidine-5-amine (197 mg, 1.273 mmol) to affords 4e, 460 mg in 94% yield. Mp: 284-285° C., $^1$H NMR (400 MHz, DMSO-d$_6$): δ 3.71 (s, 3H), 3.77 (s, 3H), 3.85 (s, 3H), 4.65 (s, 1H), 4.76-4.95 (dd, 2H, J=15.9, 16.8 Hz), 9.10 (s, 1H), 10.60 (s, 1H); $^{13}$C NMR (75 MHz, DMSO-d$_6$): δ33.4, 53.9, 54.3, 55.5, 65.1, 74.1, 82.8, 94.3, 100.4, 111.8, 114.7, 115.1, 117.9, 137.4, 146.2, 156.0, 157.2, 168.7; MS (ESI): 372 [M$^+$+H]; HRMS (ESI) calcd for C$_{18}$H$_{17}$N$_3$O$_6$Na ([M+Na]$^+$) 394.1015. found: 394.1000.

Example 4

5-(4-fluoro-3-methoxyphenyl)-2,4-dimethoxy-5,6,8,9-tetrahydrofuro[3',4':5,6]pyrido[2,3-d]pyrimidin-6-one (4d)

This compound was prepared by method described above employing 4-fluoro-3-methoxybenzaldehyde (200 mg, 0.884 mmol) tetronic acid (88 mg, 0.884 mmol) and 2,4-dimethoxypyrimidine-5-amine (137 mg, 0.884 mmol) to affords 4d, 470 mg in 97% yield. Mp: 267-270° C., $^1$H NMR (400 MHz, DMSO-d$_6$): δ 3.00 (s, 3H), 3.02 (s, 3H), 3.07 (s, 3H), 3.94-4.12 (m, 3H), 5.77-5.84 (m, 1H), 6.15-6.29 (m, 2H), 9.78 (s, 1H); $^{13}$C NMR (75 MHz, DMSO-d$_6$): δ 33.9, 53.8, 54.3, 55.8, 65.2, 93.7, 99.6, 113.2, 115.2, 115.5, 119.4, 141.1, 156.7, 157.9, 163.3, 168.7, 171.0; MS (ESI): 397 [M$^+$+Na]; HRMS (ESI) calcd for C$_{18}$H$_{16}$N$_3$O$_5$FNa ([M+Na]$^+$) 396.0971. found: 396.961.

Example 5

10-(3,4,5-trimethoxyphenyl)-6,7,9,10-tetrahydro-1H-furo[3,4-b]pyrrolo[2,3-f]quinolin-9-one (4e)

This compound was prepared by method described above employing 3,4,5-trimethoxybenzaldehyde (200 mg, 0.884 mmol) tetronic acid (88 mg, 0.884 mmol) and 2,4-dimethoxypyrimidine-5-amine (137 mg, 0.884 mmol) to affords 4e, 386 mg in 96% yield. Mp: 299-301° C., $^1$H NMR (200 MHz, DMSO-d6): δ 3.61 (s, 3H), 3.69 (s, 6H), 4.83-5.06 (dd, 2H, J=15.1, 15.1 Hz), 5.29 (s, 1H), 6.39 (br s, 1H), 6.58 (s, 2H), 6.87 (d, 1H, J=9.0 Hz), 7.25 (t, 1H, J=3.0, 2.2 Hz), 7.29 (d, 1H, J=9.0 Hz), 9.92 (s, 1H). $^{13}$C NMR (75 MHz, DMSO-d6): δ 55.7, 55.9, 59.7, 64.9, 94.7, 105.2, 109.9, 113.2, 117.3, 122.1, 129.2, 135.9, 141.9, 152.5, 157.7, 172.1. MS (ESI); 393 [M+H]$^+$. HRMS (ESI) calcd for $C_{22}H_{20}N_2O_5Na$ [M+Na]$^+$ 415.1269. found: 415.1257.

Example 6

10-(4-hydroxy-3-methoxyphenyl)-6,7,9,10-tetrahydro-1H-furo[3,4-b]pyrrolo[2,3-d]quinolin-9-one (4f)

This compound was prepared by method described above employing 4-hydroxy-3-methoxybenzaldehyde (200 mg, 1.27 mmol) tetronic acid (127 mg, 1.27 mmol) and 1H-indol-5-amine (168 mg, 1.27 mmol) to afford 4f, 440 mg in 96% yield. Mp: 301-303° C., $^1$H NMR (200 MHz, DMSO-d$_6$): δ 3.77 (s, 3H), 4.52-5.03 (dd, 2H, J=16.0, 15.3 Hz), 4.52 (s, 1H), 5.31 (s, 1H), 6.06 (d, 1H, J=8.7 Hz), 6.40-6.49 (m, 2H), 6.56 (d, 1H, J=8.7 Hz), 6.80-6.99 (dd, 1H, J=2.1, 2.1 Hz), 6.79 (t, 1H, J=2.1 Hz), 9.12 (s, 1H), 10.21 (s, 1H); $^{13}$C NMR (75 MHz, DMSO-d$_6$): δ 56.0, 64.7, 68.8, 94.9, 100.1, 104.9, 110.8, 112.3, 114.9, 120.1, 122.2, 124.4, 125.2, 127.0, 132.7, 137.8, 144.5, 146.8, 157.4, 172.4; MS (ESI): 349 [M$^+$+H].

Example 7

10-(3-hydroxy-4-methoxyphenyl)-6,7,9,10-tetrahydro-1H-furo[3,4-b]pyrrolo[2,3-f]quinolin-9-one (4g)

This compound was prepared by method described above employing 3-hydroxy-4-methoxybenzaldehyde (200 mg, 1.27 mmol) tetronic acid (127 mg, 1.27 mmol) and 1H-indol-5-amine (168 mg, 1.27 mmol) to affords 4g, 447 mg in 97% yield. Mp: 297-299° C., $^1$H NMR (200 MHz, DMSO-d$_6$): δ 3.77 (s, 3H), 4.52-5.03 (dd, 2H, J=16.0, 15.3 Hz), 4.52 (s, 1H), 5.31 (s, 1H), 6.06 (d, 1H, J=8.7 Hz), 6.40-6.49 (m, 2H), 6.56 (d, 1H, J=8.7 Hz), 6.80-6.99 (dd, 1H, J=2.1, 2.1 Hz), 6.79 (t, 1H, J=2.1 Hz), 9.12 (s, 1H), 10.21 (s, 1H); $^{13}$C NMR (75 MHz, DMSO-d$_6$): δ 37.8, 55.5, 64.7, 94.8, 99.9, 110.9, 111.2, 111.5, 113.8, 115.3, 118.3, 125.2, 127.0, 128.6, 132.7, 139.4, 145.7, 145.9, 157.3, 172.3; MS (ESI): 349 [M$^+$+H].

Example 8

10-(4-fluoro-3-methoxyphenyl)-6,7,9,10-tetrahydro-1H-furo[3,4-b]pyrrolo[2,3-f]quinolin-9-one (4h)

This compound was prepared by method described above employing 4-fluoro-3-methoxybenzaldehyde (200 mg, 0.884 mmol) tetronic acid (88 mg, 0.884 mmol) and 1H-indol-5-amine (116 mg, 0.884 mmol) to affords 4h, 441 mg in 97% yield. Mp: 170-172° C., $^1$H NMR (400 MHz, DMSO-d$_6$): δ 3.76 (s, 3H), 4.71-4.87 (dd, 2H, J=15.2, 15.2 Hz), 5.27 (s, 1H), 6.11 (br s, 1H), 6.51-6.56 (m, 1H), 6.72-6.77 (dd, 1H, J=2.6, 2.6 Hz), 6.84-6.89 (m, 1H), 7.07-7.09 (m, 2H), 7.20 (d, 1H, J=8.9 Hz), 9.78 (s, 1H), 10.92 (s, 1H); $^{13}$C NMR (75 MHz, DMSO-d$_6$): δ 55.7, 55.9, 64.8, 94.3, 100.0, 111.2, 113.1, 115.1, 115.3, 119.9, 125.5, 126.9, 128.6, 132.7, 143.2, 146.1, 146.3, 148.1, 151.3, 157.7, 172.3; MS (ESI): 351 [M$^+$+H]; HRMS (ESI) calcd for $C_{20}H_{15}N_2O_3FNa$ ([M+Na]$^+$) 373.0964. found: 373.0950.

Example 9

10-(4-methoxy-3-nitrophenyl)-6,7,9,10-tetrahydro-1H-fura[3,4-b]pyrrolo[2,3-f]quinolin-9-one (4i)

This compound was prepared by method described above employing 4-methoxy-3-nitrobenzaldehyde (200 mg, 1.105 mmol) tetronic acid (110 mg, 1.105 mmol) and 1H-indol-5-amine (145 mg, 1.105 mmol) to affords 4i, 400 mg in 96% yield. Mp: 280-281° C., $^1$H NMR (400 MHz, DMSO-d$_6$): δ 3.08 (s, 3H), 4.03-4.14 (dd, 2H, J=16.1, 16.1 Hz), 4.62 (s, 1H), 5.34 (s, 1H), 6.05 (d, 1H, J=8.7 Hz), 6.36-6.39 (m, 2H), 6.49 (d, 1H, J=8.0 Hz), 6.72-6.74 (dd, 1H, J=2.1, 1.4 Hz) 6.83 (d, 1H, J=2.1 Hz), 9.12 (s, 1H), 10.23 (s, 1H); $^{13}$C NMR (75 MHz, DMSO-d$_6$): δ 37.2, 56.4, 65.0, 93.7, 99.7, 111.3, 111.5, 112.3, 113.8, 123.5, 125.7, 126.7, 128.7, 132.7, 133.5, 138.6, 138.8, 150.2, 157.7, 172.2; MS (ESI): 429 [M$^+$+Na].

Example 10

2-methyl-10-(3,4,5-trimethoxyphenyl)-6,7,9,10-tetrahydro-1H-furo[3,4-b]pyrrolo[2,3-f]quinolin-9-one (4j)

This compound was prepared by method described above employing 3,4,5-trimethoxybenzaldehyde (200 mg, 1.020 mmol) tetronic acid (102 mg, 1.020 mmol) and 2-methyl-1H-indol-5-amine (193 mg, 1.020 mmol) to affords 4j, 409 mg in 98% yield. Mp: 280-281° C., $^1$H NMR (400 MHz, DMSO-d$_6$): δ 2.27 (s, 3H), 3.55 (s, 3H), 3.63 (s, 6H), 4.77-4.94 (dd, 2H, J=15.2, 15.2 Hz), 5.13 (s, 1H), 6.00 (br s, 1H), 6.48 (s, 2H), 6.69 (d, 1H, J=8.9 Hz), 7.13 (d, 1H, J=8.0 Hz), 9.83 (s, 1H), 10.85 (s, 1H); $^{13}$C NMR (75 MHz, DMSO-d$_6$): δ 13.3, 38.5, 55.7, 59.7, 64.8, 94.4, 98.2, 105.2, 109.9, 110.1, 112.4, 128.0, 128.6, 132.8, 135.6, 135.7, 142.2, 152.3, 157.7, 172.3; MS (ESI): 401 [M$^+$+Na]; HRMS (ESI) calcd for $C_{20}H_{15}N_3O_5Na$ ([M+Na]$^+$) 400.0909. found: 400.0911.

Example 11

10-(3-hydroxy-4-methoxyphenyl)-2-methyl-6,7,9,10-tetrahydro-1H-furo[3,4-b]pyrrolo[2,3-f]quinolin-9-one (4k)

This compound was prepared by method described above employing 3-hydroxy-4-methoxybenzaldehyde (200 mg, 1.273 mmol) tetronic acid (127 mg, 1.273 mmol) and 2-methyl-1H-indol-5-amine (242 mg, 1.273 mmol) to affords 4k, 349 mg in 96 yield. Mp: 293-294° C., $^1$H NMR (300 MHz, DMSO-d$_6$): δ 2.25 (s, 3H), 3.65 (s, 3H) 4.77-4.89 (dd, 2H, J=15.4, 15.4 Hz), 5.02 (s, 1H), 5.85 (s, 1H), 6.52 (d, 1H, J=1.8 Hz), 6.60-6.64 (dd, 1H, J=1.8, 2.0 Hz), 6.67-6.72 (m, 2H), 7.11 (d, 1H, J=8.4 Hz), 8.67 (s, 1H), 9.78 (s, 1H), 10.81 (s, 1H); $^{13}$C NMR (75 MHz, DMSO-d$_6$): δ 13.3, 37.7, 55.5, 64.7, 94.7, 98.1, 109.9, 111.5, 113.0, 115.2, 118.3, 127.9, 128.5, 132.8, 135.6, 139.4, 145.7, 145.9, 157.2, 172.3; MS (ESI): 363 [M$^+$+H]; HRMS (ESI) calcd for $C_{21}H_{13}N_2O_4Na$ ([M+Na]$^+$) 385.1164. found: 385.1152.

Example 12

10-(4-fluoro-3-methoxyphenyl)-2-methyl-6,7,9,10-tetrahydro-1H-furo[3,4-b]pyrrolo[2,3-f]quinolin-9-one (4l)

This compound was prepared by method described above employing 4-fluoro-3-methoxybenzaldehyde (200 mg, 1.298 mmol) tetronic acid (129 mg, 1.298 mmol) and 2-methyl-1H-indol-5-amine (246 mg, 1.298 mmol) to affords 4l, 461 mg in 97% yield. Mp: 198-199° C., $^1$H NMR (400 MHz, DMSO-d$_6$): δ 2.80 (s, 3H), 4.30 (s, 3H), 5.22-5.32 (dd, 2H, J=15.5, 15.5 Hz), 5.73 (s, 1H), 6.27 (s, 1H), 7.04-7.07 (m, 1H), 7.16 (d, 1H, J=8.6 Hz), 7.32-7.37 (dd, 1H, J=7.7, 7.7 Hz), 7.55 (d, 1H, J=6.9 Hz), 7.61 (d, 1H, J=8.6 Hz), 10.13 (s, 1H), 11.13 (s, 1H); $^{13}$C NMR (75 MHz, DMSO-d$_6$): δ 13.2, 18.4, 38.0, 55.8, 64.7, 94.2, 98.0, 110.0, 112.1, 113.4, 115.2, 119.8, 127.9, 128.6, 132.8, 135.8, 143.1, 146.2, 157.5, 172.3; MS (ESI): 365 [M$^+$+H].

Example 13

10-(2-fluoro-4-methoxyphenyl)-2-methyl-6,7,9,10-tetrahydro-1H-furo[3,4-b]pyrrolo[2,3-f]quinolin-9-one (4m)

This compound was prepared by method described above employing 2-fluoro-4-methoxybenzaldehyde (200 mg, 1.298 mmol) tetronic acid (129 mg, 1.298 mmol) and 2-methyl-1H-indol-5-amine (246 mg, 1.298 mmol) to affords 4m, 469 mg in 99% yield. Mp: 205-207° C., $^1$H NMR (400 MHz, DMSO-d$_6$): δ 2.80 (s, 3H), 4.30 (s, 3H), 5.22-5.32 (dd, 2H, J=15.5, 15.5 Hz), 5.73 (s, 1H), 6.27 (s, 1H), 7.04-7.07 (m, 3H), 7.16 (d, 1H, J=8.6 Hz), 7.61 (d, 1H, J=8.6 Hz), 10.13 (s, 1H), 11.13 (s, 1H); $^{13}$C NMR (75 MHz, DMSO-d$_6$): δ 13.2, 18.4, 38.0, 55.8, 64.7, 94.2, 98.0, 110.0, 112.1, 113.4, 115.2, 119.8, 127.9, 128.6, 132.8, 135.8, 143.1, 146.2, 157.5, 172.3; MS (ESI): 365 [M$^+$+H].

Example 14

10-(3,4,5-trimethoxyphenyl)-6,7,9,10-tetrahydro-1H-furo[3,4-b]pyrazolo[3,4-f]quinolin-9-one (4n)

This compound was prepared by method described above employing 3,4,5-trimethoxybenzaldehyde (200 mg, 1.020 mmol) tetronic acid (102 mg, 1.020 mmol) and 1H-indazol-5-amine (135 mg, 1.020 mmol) to affords 4n, 329 mg in 97% yield. Mp: 278-279° C., $^1$H NMR (300 MHz, DMSO-d$_6$): δ 3.56 (s, 3H), 3.66 (s, 6H), 4.80-5.05 (dd, 2H, J=15.3, 16.0 Hz), 5.35 (s, 1H), 6.59 (s, 2H), 7.09 (d, 1H, J=8.7 Hz), 7.42 (d, 1H, J=8.7 Hz), 7.96 (s, 1H); $^{13}$C NMR (75 MHz, DMSO-d$_6$): δ 38.5, 55.7, 59.7, 64.8, 94.5, 100.1, 105.3, 111.1, 111.3, 113.3, 125.4, 127.0, 128.6, 132.7, 142.3, 152.3, 157.8, 172.4; MS (ESI): 604 [M$^+$+H].

Example 15

10-(4-hydroxy-3-methoxyphenyl)-6,7,9,10-tetrahydro-1H-furo[3,4-b]pyrazolo[3,4-f]quinolin-9-one (4o)

This compound was prepared by method described above employing 4-hydroxy-3-methoxybenzaldehyde (200 mg, 1.273 mmol) tetronic acid (127 mg, 1.273 mmol) and 1H-indazol-5-amine (168 mg, 1.273 mmol) to affords 4o, 439 mg in 95% yield. Mp: 238-240° C., $^1$H NMR (400 MHz, DMSO-d$_6$): δ 3.73 (s, 3H), 4.77-4.89 (dd, 2H, J=14.7, 15.6 Hz), 5.27 (s, 1H), 6.49-6.58 (m, 2H), 6.91 (s, 1H), 7.02 (d, 1H, J=8.7 Hz), 7.34 (d, 1H, J=8.7 Hz), 7.72 (s, 1H), 9.89 (s, 1H); $^{13}$C NMR (75 MHz, DMSO-d$_6$): δ 37.8, 55.6, 64.9, 95.1, 109.8, 112.3, 113.9, 115.2, 117.3, 120.2, 122.2, 129.2, 132.2, 137.3, 137.5, 144.8, 147.0, 157.5, 172.3; MS (ESI): 350 [M$^+$+H]; HRMS (ESI) calcd for C$_{19}$H$_{15}$N$_3$O$_4$Na ([M+Na]$^+$) 372.0960. found: 372.0954.

Example 16

10-(3-hydroxy-4-methoxyphenyl)-6,7,9,10-tetrahydro-1H-furo[3,4-b]pyrazolo[3,4-f]quinolin-9-one (4p)

This compound was prepared by method described above employing 3-hydroxy-4-methoxybenzaldehyde (200 mg, 1.273 mmol) tetronic acid (127 mg, 1.273 mmol) and 1H-indazol-5-amine (168 mg, 1.273 mmol) to affords 4p, 442 mg in 96% yield. Mp: 243-245° C., $^1$H NMR (400 MHz, DMSO-d$_6$): δ 3.73 (s, 3H), 4.77-4.89 (dd, 2H, J=14.7, 15.6 Hz), 5.27 (s, 1H), 6.49-6.58 (m, 2H), 6.91 (s, 1H), 7.02 (s, 1H, J=8.7 Hz), 7.34 (d, 1H, J=8.7 Hz), 7.72 (s, 1H), 9.89 (s, 1H); $^{13}$C NMR (75 MHz, DMSO-d$_6$): δ 37.7, 55.5, 64.9, 95.0, 109.8, 111.6, 113.8, 115.3, 117.3, 118.4, 122.2, 129.2, 132.1, 137.3, 139.0, 146.1, 146.1, 157.4, 172.2; MS (ESI): 350 [M$^+$+H]; HRMS (ESI) calcd for C$_{19}$H$_{15}$N$_3$O$_4$Na ([M+Na]$^+$) 372.0960. found: 372.0954.

Example 17

10-(4-fluoro-3-methoxyphenyl)-6,7,9,10-tetrahydro-1H-furo[3,4-b]pyrazolo[3,4-f]quinolin-9-one (4q)

This compound was prepared by method described above employing 4-fluoro-3-methoxybenzaldehyde (200 mg, 0.884 mmol) tetronic acid (88 mg, 0.884 mmol) and 1H-indazol-5-amine (116 mg, 0.884 mmol) to affords 4q, 433 mg in 95% yield. Mp: 307-309° C., $^1$H NMR (300 MHz, DMSO-d$_6$): δ 3.79 (s, 3H), 4.85-5.01 (dd, 2H, J=15.6, 15.6 Hz), 5.42 (s, 1H), 6.64-6.69 (m, 1H), 6.97-7.08 (m, 2H), 722-7.26 (dd, 1H, J=1.8, 1.8 Hz), 7.39 (d, 1H, J=8.8 Hz), 7.87 (s, 1H), 10.0 (s, 1H); $^{13}$C NMR (75 MHz, DMSO-d$_6$): δ 42.8, 60.8, 69.9, 99.5, 118.0, 118.4, 120.3, 120.5, 122.3, 124.9, 127.0, 134.2, 147.8, 147.9, 151.2, 153.6, 156.0, 162.7, 177.1; MS (ESI): 352 [M$^+$+H]; HRMS (ESI) calcd for C$_{19}$H$_{14}$N$_3$O$_3$FNa ([M+Na]$^+$) 374.0916. found: 374.0900.

Example 18

10-(4-methoxy-3-nitrophenyl)-6,7,9,10-tetrahydro-1H-furo[3,4-b]pyrazolo[3,4-f]quinolin-9-one (4r)

This compound was prepared by method described above employing 4-methoxy-3-nitrobenzaldehyde (200 mg, 1.104 mmol) tetronic acid (110 mg, 1.104 mmol) and 1H-indazol-5-amine (146 mg, 1.104 mmol) to affords 4r, 345 mg in 94% yield. Mp: 217-218° C., $^1$H NMR (400 MHz, DMSO-d$_6$): δ 3.22 (s, 3H), 4.10-4.23 (dd, 2H, J=15.2, 16.1 Hz), 4.85 (s, 1H), 6.39 (d, 1H, J=8.0 Hz), 6.47 (d, 1H, J=8.0 Hz), 6.60-6.73 (m, 3H), 6.88-6.98 (m, 2H), 7.38 (s, 1H), 9.27 (s, 1H), 12.19 (s, 1H); $^{13}$C NMR (75 MHz, DMSO-d$_6$): δ 37.0, 56.4, 65.0, 94.1, 1112, 114.0, 117.3, 123.5, 129.3, 133.5, 138.4, 150.4, 157.9, 181.0; MS (ESI): 379 [M$^+$+H]; HRMS (ESI) calcd for C$_{19}$H$_{14}$N$_4$O$_5$Na ([M+Na]$^+$) 413.3007. found: 413.2712.

Example 19

10-(3,4,5-trimethoxyphenyl)-6,7,9,10-tetrahydrofuro[3,4-b][1,3]thiazolo[5,4-f]quinolin-9-one (4s)

This compound was prepared by method described above employing 3,4,5-trimethoxybenzaldehyde (200 mg, 1.020 mmol) tetronic acid (102 mg, 1.020 mmol) and benzo[d]thiazol-5-amine (153 mg, 1.020 mmol) to affords 4s, 393 mg in 94% yield. Mp: 309-310° C., $^1$H NMR (400 MHz, DMSO-$d_6$): δ 3.59 (s, 3H), 3.67 (s, 6H), 4.86-5.00 (dd, 2H, J=16.1, 16.1 Hz), 5.09 (s, 1H), 6.48 (s, 2H), 7.22 (d, 1H, J=8.7 Hz), 7.92 (d, 1H, J=8.7 Hz), 9.06 (s, 1H), 10.33 (s, 1H); $^{13}$C NMR (300 MHz, DMSO-$d_6$): δ 40.9, 55.7, 59.8, 64.9, 95.5, 105.9, 116.1, 116.2, 122.4, 134.0, 135.1, 136.2, 138.9, 149.4, 152.5, 153.7, 157.2, 171.6; MS (EST): 411 [M$^+$+H]; HRMS (ESI) calcd for $C_{21}H_{19}N_2O_5$ ([M]$^+$) 411.1014. found: 411.1021.

Example 20

10-(4-hydroxy-3-methoxyphenyl)-6,7,9,10-tetrahydrofuro[3,4-b][1,3]thiazolo[5,4-f]quinolin-9-one (4t)

This compound was prepared by method described above employing 4-hydroxy-3-methoxybenzaldehyde (200 mg, 1.315 mmol) tetronic acid (131 mg, 1.315 mmol) and benzo[d]thiazol-5-amine (197 mg, 1.315 mmol) to affords 4t, 367 mg in 96% yield. Mp: 296-297° C., $^1$H NMR (400 MHz, DMSO-$d_6$): δ 3.70 (s, 3H), 4.786-5.01 (dd, 2H, J=15.5, 16.4 Hz), 5.04 (s, 1H), 6.49-6.52 (dd, 1H, J=1.7, 2.5 Hz), 6.60 (d, 1H, J=8.6 Hz), 6.87 (d, 2H, J=1.7 Hz), 7.20 (d, 1H, J=8.6 Hz), 7.93 (d, 1H, J=8.6 Hz), 8.85 (s, 1H), 10.34 (s, 1H); $^{13}$C NMR (75 MHz, DMSO-$d_6$): δ 55.5, 64.8, 96.0, 112.9, 115.2, 116.0, 116.8, 120.7, 122.2, 134.0, 134.5, 135.1, 145.2, 146.9, 149.4, 153.6, 156.8, 171.6; MS (ESI): 367 [M$^+$+H], HRMS (ESI) calcd for $C_{19}H_{14}N_2O_4NaS$ ([M+Na]$^+$) 389.0571. found: 389.0564.

Example 21

10-(3-hydroxy-4-methoxyphenyl)-6,7,9,10-tetrahydrofuro[3,4-b][1,3]thiazolo[5,4-f]quinolin-9-one (4u)

This compound was prepared by method described above employing 3-hydroxy-4-methoxybenzaldehyde (200 mg, 1.315 mmol) tetronic acid (131 mg, 1.315 mmol) and benzo[d]thiazol-5-amine (197 mg, 1.315 mmol) to affords 4u, 452 mg in 90% yield. Mp: 327-329° C., $^1$H NMR (300 MHz, DMSO-$d_6$): δ 3.67 (s, 3H), 4.86-5.00 (m, 3H), 6.57-6.65 (m, 2H), 6.77 (d, 1H, J=8.3 Hz), 7.22 (d, 1H, J=8.6 Hz), 7.93 (d, 1H, J=8.4 Hz), 8.84 (br s, 1H), 9.08 (s, 1H), 10.34 (s, 1H); $^{13}$C NMR (75 MHz, DMSO-$d_6$): δ 40.0, 55.4, 64.8, 96.0, 111.5, 115.6, 115.9, 116.8, 119.2, 122.2, 134.1, 135.1, 136.0, 146.1, 146.4, 149.4, 153.6, 156.7, 171.6; MS (ESI): 367 [M$^+$+H]; HRMS (ESI) calcd for $C_{19}H_{14}N_2O_4NaS$ ([M+Na]$^+$) 389.0571. found: 389.0550.

Example 22

10-(4-hydroxy-3-methoxyphenyl)-2-methyl-6,7,9,10-tetrahydrofuro[3,4-b][1,3]thiazolo[5,4-f]quinolin-9-one (4v)

This compound was prepared by method described above employing 4-hydroxy-3-methoxybenzaldehyde (200 mg, 1.273 mmol) tetronic acid (127 mg, 1.273 mmol) and 2-methylbenzo[d]thiazol-5-amine (208 mg, 1.273 mmol) to affords 4v, 357 mg in 95% yield. Mp: 293-295° C., $^1$H NMR (400 MHz, DMSO-$d_6$): δ 1.89 (s, 3H), 3.84 (s, 3H), 4.02-4.20 (dd, 2H, J=15.2, 16.1 Hz), 4.64 (s, 1H), 5.55-5.58 (dd, 1H, J=1.7, 1.7 Hz), 5.69 (d, 1H, J=8.0 Hz), 6.19-6.21 (m, 2H), 6.95 (d, 1H, J=8.9 Hz), 7.85 (s, 1H), 9.32 (s, 1H); $^{13}$C NMR (75 MHz, DMSO-$d_6$): δ 36.6, 40.3, 55.8, 56.5, 65.5, 96.8, 112.7, 114.8, 115.5, 117.3, 120.0, 121.1, 135.4, 137.7, 145.2, 147.2, 152.3, 158.7, 167.5, 172.63; MS (ESI): 381 [M$^+$+H]; HRMS (ESI) calcd for $C_{20}H_{16}N_2O_4NaS$ ([M+Na]$^+$) 403.0728. found: 403.0710.

Example 23

10-(3-methoxy-4-nitrophenyl)-2-methyl-6,7,9,10-tetrahydrofuro[3,4-b][1,3]thiazolo[5,4-f]quinolin-9-one (4w).

This compound was prepared by method described above employing 3-methoxy-4-nitrobenzaldehyde (200 mg, 1.104 mmol) tetronic acid (110 mg, 1.104 mmol) and 2-methylbenzo[d]thiazol-5-amine (182 mg, 1.104 mmol) to affords 4w, 430 mg in 95% yield. Mp: 190-191° C., $^1$H NMR (400 MHz, DMSO-$d_6$): δ 2.71 (s, 3H), 3.83 (s, 3H), 4.80-4.96 (dd, 2H, J=15.5, 16.4 Hz), 5.64 (s, 1H), 7.00-7.08 (m, 2H), 7.49-7.51 (dd, 1H, J=2.5, 2.5 Hz), 7.66-7.71 (m, 2H), 8.08 (s, 1H), 10.11 (s, 1H); $^{13}$C NMR (75 MHz, DMSO-$d_6$): δ 19.9, 35.9, 55.9, 56.4, 65.1, 95.2, 113.8, 114.4, 115.1, 121.3, 123.7, 129.6, 133.4, 134.9, 138.4, 150.4, 158.3, 167.7, 171.7; MS (ESI): 410 [M$^+$+H]; HRMS (ESI) calcd for $C_{20}H_{15}N_3O_5NaS$ ([M+Na]$^+$) 432.0630. found: 432.0610.

Example 24

10-(3-hydroxy-4-methoxyphenyl)-2-sulfanyl-6,7,9,10-tetrahydro-1H-furo[3,4-b]imidazo[4,5-f]quinolin-9-one (4x)

This compound was prepared by method described above employing 3-hydroxy-4-methoxybenzaldehyde (200 mg, 1.273 mmol) tetronic acid (127 mg, 1.273 mmol) and 5-amine-1H-benzo[d]imidazole-2-thiol (210 mg, 1.273 mmol) to affords 4x, 452 mg in 90% yield. Mp: 334-337° C., $^1$H NMR (400 MHz, DMSO-$d_6$): δ 4.00 (s, 3H), 7.07-7.17 (m, 4H), 7.49 (d, J=8.9 Hz), 8.19-8.22 (dd, 1H, J=2.2, 2.2 Hz), 8.40 (d, 1H, J=2.2 Hz), 8.69 (s, 1H), 12.58 (s, 1H), 12.63 (s, 1H); $^{13}$C NMR (75 MHz, DMSO-$d_6$): δ 55.6, 69.0, 103.9, 105.2, 111.3, 111.5, 117.1, 121.1, 122.8, 124.5, 133.5, 137.5, 145.9, 147.5, 148.3, 149.2, 162.5, 167.8, 173.5; MS (ESI): 381 [M$^+$+H].

Example 25

10-(3,4,5-trimethoxyphenyl)-6,7,9,10-tetrahydro-1H-furo[3,4-b][1,2,3]triazolo[4,5-f]quinolin-9-one (4y)

This compound was prepared by method described above employing 3,4,5-trimethoxybenzaldehyde (200 mg, 1.020 mmol) tetronic acid (102 mg, 1.020 mmol) and 1H-benzo[d][1,2,3]triazol-5-amine (136 mg, 1.020 mmol) to affords 4y, 378 mg in 94% yield. Mp: 324-325° C., NMR (400 MHz, DMSO-$d_6$): δ 3.56 (s, 3H), 3.66 (s, 6H), 4.88-5.14 (dd, 2H, J=15.6, 15.6 Hz), 5.27 (s, 1H), 6.59 (s, 2H), 7.12 (d, 1H, J=8.5 Hz), 7.87 (d, 1H, J=8.5 Hz), 10.41 (s, 1H); $^{13}$C NMR (75 MHz, DMSO-$d_6$): δ 36.7, 55.7, 59.7, 65.1, 96.0, 104.8, 115.2, 118.3, 132.6, 135.3, 136.1, 140.2, 141.6, 152.6, 158.0, 171.8; MS (ESI): 395 [M$^+$+H]; HRMS (ESI) calcd for $C_{20}H_8N_3O_5Na$ ([M+Na]$^+$) 417.1174. found: 417.1176.

Example 26

10-(2-fluoro-4-methoxyphenyl)-6,7,9,10-tetrahydro-1H-furo[3,4-b][1,2,3]triazolo[4,5-f]quinolin-9-one (4z)

This compound was prepared by method described above employing 2-fluoro-4-methoxybenzaldehyde (200 mg, 0.884 mmol) tetronic acid (88 mg, 0.884 mmol) and 1H-benzo[d][1,2,3]triazol-5-amine (118 mg, 0.884 mmol) to affords 4z, 439 mg in 96% yield. Mp: 308-310° C., $^1$H NMR (400 MHz, DMSO-d$_6$): δ 3.68 (s, 3H), 4.85-4.95 (dd, 2H, J=15.6, 15.6 Hz), 5.06 (s, 1H), 6.55-6.61 (m, 2H), 7.08 (d, 1H, J=8.7 Hz), 7.20 (br s, 1H), 7.69-7.71 (m, 1H), 10.29 (s, 1H); $^{13}$C NMR (300 MHz, DMSO-d$_6$): δ 29.8, 55.3, 65.0, 94.6, 101.5, 101.8, 109.8, 111.6, 115.0, 118.2, 130.6, 130.9, 158.9, 159.3, 171.6; MS (ESI): 353 [M$^+$+H]; HRMS (ESI) calcd for $C_{18}H_{13}N_4O_3FNa$ ([M+Na]$^+$) 375.0869. found: 375.0870.

Example 27

3-(4-methoxyphenyl)-4-(3,4,5-trimethoxyphenyl)-4,5,7,8-tetrahydrofuro[3',4':5,6]pyrido[3,2-d]isoxazol-5-one (4aa)

This compound was prepared by method described above employing 3,4,5-trimethoxybenzaldehyde (200 mg, 1.020 mmol) tetronic acid (102 mg, 1.020 mmol) and 3-(4-methoxyphenyl)isoxazol-5-amine (193 mg, 1.020 mmol) to affords 4aa, 436 mg in 94% yield. Mp: 218-219° C., $^1$H NMR (400 MHz, DMSO-d$_6$): δ 3.54 (s, 3H), 3.59 (s, 6H), 3.75 (s, 3H), 4.89-5.04 (dd, 2H, J=16.4, 16.4 Hz), 5.23 (s, 1H), 6.40 (s, 2H), 6.94 (d, 2H, J=8.6 Hz), 7.52 (d, 2H, J=8.6 Hz), 11.53 (s, 1H); $^{13}$C NMR (75 MHz, DMSO-d$_6$): δ 35.1, 55.6, 59.7, 64.9, 94.1, 100.8, 105.1, 127.2, 128.6, 129.3, 134.6, 136.0, 138.9, 152.3, 157.4, 159.7, 161.8, 170.7; MS (EST): 451 [M$^+$+H]; HRMS (ESI) calcd for $C_{24}H_{22}N_2O_7Na$ ([M+Na]$^+$) 473.1324. found: 473.1330.

Example 28

4-(3-hydroxy-4-methoxyphenyl)-3-(4-methoxyphenyl)-4,5,7,8-tetrahydrofuro[3',4':5,6]pyrido[3,2-d]isoxazol-5-one (4ab).

This compound was prepared by method described above employing 3-hydroxy-4-methoxybenzaldehyde (200 mg, 1.273 mmol) tetronic acid (127 mg, 1.273 mmol) and 3-(4-methoxyphenyl)isoxazol-5-amine (242 mg, 1.273 mmol) to affords 4ab, 363 mg in 97% yield. Mp: 219-221° C., $^1$H NMR (200 MHz, DMSO-d$_6$): δ 3.71 (s, 3H), 3.78 (s, 3H), 4.69-4.78 (m, 3H), 6.23 (br s, 1H), 6.44 (d, 1H, J=8.0 Hz), 6.51 (s, 1H), 4.98 (s, 1H), 6.78 (d, 1H, J=8.9 Hz), 6.98 (d, 2H, J=8.9 Hz), 7.39 (d, 2H, J=8.0 Hz), 8.85 (s, 1H); $^{13}$C NMR (75 MHz, DMSO-d$_6$): δ 55.0, 55.5, 66.6, 89.2, 100.9, 111.9, 114.0, 114.8, 117.6, 122.2, 129.4, 131.9, 145.9, 146.0, 146.1, 159.8, 162.9, 167.7, 174.6; MS (ESI): 407 [M$^+$+H]; HRMS (EST) calcd for $C_{22}H_{20}N_2O_6Na$ ([M+Na]$^+$) 437.3970. found: 437.1845.

Example 29

3-(4-chlorophenyl)-4-(3,4,5-trimethoxyphenyl)-4,5,7,8-tetrahydrofuro[3',4':5,6]pyrido[3,2-d]isoxazol-5-one (4ac)

This compound was prepared by method described above employing 3,4,5-trimethoxybenzaldehyde (200 mg, 1.020 mmol) tetronic acid (102 mg, 1.020 mmol) and 3-(4-chlorophenyl)isoxazol-5-amine (197 mg, 1.020 mmol) to affords 4ac, 459 mg in 85% yield. Mp: 248-249° C., $^1$H NMR (400 MHz, DMSO-d$_6$): δ 3.54 (s, 3H), 3.59 (s, 6H), 4.89-5.05 (dd, 2H, J=16.1, J=16.1 Hz), 5.25 (s, 1H), 6.38 (s, 2H), 7.44 (d, 2H, J=8.0 Hz), 7.60 (d, 2H, 8.0 Hz), 11.62 (s, 1H). $^{13}$C NMR (75 MHz, DMSO-d$_6$): δ 35.2, 55.1, 55.6, 59.8, 64.8, 81.1, 89.1, 100.8, 105.1, 114.0, 129.0, 139.2, 147.3, 152.4, 160.3, 161.7, 169.9, 170.3. MS (EST): 455 [M$^+$+H]. HRMS (ESI) calcd for $C_{23}H_{19}N_2O_6NaCl$ ([M+Na]$^+$) 477.0829. found: 477.0809.

Example 30

3-(4-chlorophenyl)-4-(3-hydroxy-4-methoxyphenyl)-4,5,7,8-tetrahydrofuro[3',4':5,6]pyrido[3,2-d]isoxazol-5-one (4ad)

This compound was prepared by method described above employing 3-hydroxy-4-methoxybenzaldehyde (200 mg, 1.273 mmol) tetronic acid (127 mg, 1.273 mmol) and 3-(4-chlorophenyl)isoxazol-5-amine (246 mg, 1.273 mmol) to affords 4ad, 378 mg in 97% yield. Mp: 245-246° C., $^1$H NMR (300 MHz, DMSO-d$_6$): δ 3.72 (s, 3H), 4.67-4.79 (dd, 2H, J=16.6, 16.2 Hz), 4.92 (s, 1H), 6.55-6.64 (m, 3H), 7.24 (d, 2H, J=8.4 Hz), 7.39 (d, 2H, J=8.4 Hz), 8.32 (s, 1H), 11.16 (s, 1H); $^{13}$C NMR (75 MHz, DMSO-d$_6$): δ 34.4, 55.4, 64.6, 94.1, 101.7, 111.4, 115.1, 118.4, 127.0, 128.3, 128.6, 129.0, 134.6, 136.1, 146.0, 146.3, 156.3, 159.4, 162.2, 167.1, 170.7; MS (ESI): 433 [M$^+$+Na]; HRMS (EST) calcd for $C_{21}H_{15}N_2O_5NaCl$ ([M+Na]$^+$) 433.0567. found: 433.0554.

Example 31

9-(4-hydroxy-3-methoxyphenyl)-5,6,7-trimethoxy-1,3,4,9-tetrahydrofuro[3,4-b]quinolin-1-one (4ae)

This compound was prepared by method described above employing 4-hydroxy-3-methoxybenzaldehyde (200 mg, 1.273 mmol) tetronic acid (127 mg, 1.273 mmol) and 3,4,5-trimethoxybenzenamine (232 mg, 1.273 mmol) to affords 4ae, 447 mg, 85% yield. Mp: 290-291° C., $^1$H NMR (400 MHz, DMSO-d$_6$): δ 3.38 (s, 3H), 3.63 (s, 3H), 3.70 (s, 3H), 3.78 (s, 3H), 4.75-4.91 (m, 3H), 6.37-6.41 (m, 2H), 6.60 (d, 1H, J=7.5 Hz), 6.76 (d, 1H, J=1.5 Hz), 8.72 (s, 1H), 9.86 (s, 1H); $^{13}$C NMR (75 MHz, DMSO-d$_6$): δ 34.7, 55.6, 59.9, 60.2, 64.8, 95.4, 96.2, 110.4, 112.0, 115.0, 119.7, 133.0, 137.4, 138.2, 144.6, 146.8, 151.7, 152.6, 157.4, 172.1; MS (ESI): 400 [M$^+$+H].

Biological Activity

In Vitro Evaluation of Anticancer Activity

Compounds 4a-4z and 4aa-4ae have been evaluated for their in vitro cytotoxicity in selected human cancer cell lines i.e., colon (Colo205), lung (Hop-62, A549), cervix (SiHa), prostate (PC3), oral (KB, DWD, Gurav), Ovarian (A-2780) and breast (MCF7, Zr-75-1) origin by employing the sulforhodamine B (SRB) assay method (Skehn, P.; Storeng, R.; Scudiero, A.; Monks, J.; MeMohan, D.; Vistica, D.; Jonathan, T. W.; Bokesch, H.; Kenney, S.; Boyd M. R. *J. Natl. Cancer Inst.* 1990, 82, 1107). The results are summarized with podophyllotoxin and standard drug Adriamycin in Table 1. All the new compounds were significantly cytotoxic towards the colon (Colo205), breast (MCF7, Zr-75-1), lung (Hop-62, A549), oral (KB, DWD, Gurav), cervix (SiHa), prostate (PC3), and ovarian (A-2780) cell lines compared to the standard drug tested, with the concentration of the drug that produced 50% inhibition of cell growth ($GI_{50}$).

Procedure of the SRB-Assay

The synthesized compounds have been evaluated for their in vitro cytotoxicity in human cancer cell lines. A protocol of 48 h continuous drug exposure has been used and a sulforhodamine B (SRB) protein assay has been used to estimate cell viability or growth. The cell lines were grown in DMEM medium containing 10% fetal bovine serum and 2 mM L-glutamine and were inoculated into 96 well microtiter plates in 90 mL at plating densities depending on the doubling time of individual cell lines. The microliter plates were incubated at 37_C, 5% CO2, 95% air, and 100% relative humidity for 24 h prior to addition of experimental drugs. Aliquots of 10 mL of the drug dilutions were added to the appropriate microliter wells already containing 90 mL of cells, suiting in the required final drug concentrations. For each compound four concentrations (0.1, 1, 10 and 100 uM) were evaluated and each was done in triplicate wells. Plates were incubated further for 48 h and assay was terminated by the addition of 50 mL of cold trichloro acetic acid (TCA) (final concentration, 10% TCA) and incubated for 60 min at 4_C. The plates were washed five times with tap water and airdried. Sulforhodamine B (SRB) solution (50 mL) at 0.4% (w/v) in 1% acetic acid was added to each of the cells, and plates were incubated for 20 min at room temperature. The residual dye was removed by washing five times with 1% acetic acid. The plates were airdried. Bound stain was subsequently eluted with 10 mM trizma base, and the absorbance was read on an ELISA plate reader at a wavelength of 540 nm with 690 nm reference wavelengths. Percent growth was calculated on a plate by plate basis for test wells relative to control wells. The above determinations were repeated three times. Percentage growth was expressed as the (ratio of average absorbance of the test well to the average absorbance of the control wells)*100. Growth inhibition of 50% (GI50) was calculated from [(Ti−Tz)/(C−Tz)]*100 ¼ 50, which is the drug concentration resulting in a 50% reduction in the net protein increase (as measured by SRB staining) in control cells during the drug incubation. Where, Tz ¼ Optical density at time zero, OD of control ¼ C, and OD of test growth in the presence of drug ¼ Ti.

TABLE 1

In vitro anticancer activity ($GI_{50}$ μM) data for some representative compounds

| Compd | Breast | | Oral | | | Colon | Lung | | Prostate | Cervix | Ovarian |
|---|---|---|---|---|---|---|---|---|---|---|---|
| | Zr-75-1 | MCF7 | KB | Gurav | DWD | Colo 205 | A-549 | Hop62 | PC3 | SiHa | A-2780 |
| 4a | 2.2 | 2.4 | 0.17 | 2.0 | 2.4 | 0.16 | 2.1 | 2.5 | 2.4 | — | — |
| 4b | — | — | — | — | — | — | — | 2.7 | — | — | — |
| 4c | — | — | — | — | — | — | — | 2.8 | — | — | — |
| 4d | — | — | 2.2 | — | — | — | 2.6 | — | — | — | — |
| 4e | 2.8 | — | 2.0 | — | 2.8 | 2.3 | 2.4 | — | — | — | 2.7 |
| 4f | 2.0 | 2.3 | — | 2.6 | 2.4 | 2.5 | — | — | — | — | — |
| 4g | 2.8 | 2.9 | 2.2 | 2.3 | — | 0.19 | 2.3 | 2.2 | — | — | 2.7 |
| 4h | 2.5 | 2.1 | 0.17 | 2.5 | 2.6 | — | 2.2 | 2.6 | — | — | 2.3 |
| 4i | — | — | — | — | — | 2.4 | — | — | — | — | — |
| 4j | — | — | — | — | — | — | — | — | — | 2.6 | — |
| 4k | 0.17 | 2.0 | 2.1 | 0.17 | 2.0 | 2.7 | <0.1 | 0.16 | 0.17 | — | 0.19 |
| 4l | — | 2.6 | — | 2.5 | 2.1 | — | — | 2.4 | — | — | 2.4 |
| 4m | — | <0.1 | — | — | — | — | — | — | — | — | — |
| 4n | 0.16 | 0.19 | 2.1 | 0.16 | <0.1 | 2.7 | <0.1 | 2.1 | 0.19 | 0.19 | 0.14 |
| 4o | 2.1 | 2.0 | — | — | — | 2.0 | — | 2.8 | 2.3 | — | — |
| 4p | — | — | — | — | — | 2.6 | — | 2.6 | — | — | — |
| 4q | — | 2.7 | — | 2.6 | — | — | 2.3 | — | — | — | — |
| 4r | 0.14 | 0.16 | 0.12 | 0.14 | <0.1 | 2.2 | <0.1 | 0.13 | 0.16 | — | 0.13 |
| 4s | 2.1 | — | 2.1 | — | 2.5 | 2.5 | 2.4 | — | — | — | 2.3 |
| 4t | <0.1 | 0.15 | 0.15 | 0.14 | <0.1 | 2.2 | <0.1 | 0.12 | 0.16 | — | 0.15 |
| 4u | 0.16 | 0.18 | 0.18 | 0.19 | 2.0 | 0.15 | <0.1 | 2.3 | 2.1 | 2.0 | 0.18 |
| 4v | 0.17 | 0.16 | 2.0 | 0.18 | <0.1 | — | <0.1 | 0.17 | 0.16 | 0.18 | 0.12 |
| 4w | — | 0.15 | — | — | — | — | — | — | — | — | — |
| 4x | — | 2.7 | — | — | — | — | — | — | — | — | — |
| 4y | — | — | 2.9 | — | — | — | — | — | — | — | — |
| 4z | — | <0.1 | — | — | — | — | — | — | — | — | — |
| 4aa | — | — | — | — | — | — | — | 2.5 | — | — | — |
| 4ab | 0.14 | 0.19 | 0.17 | 0.14 | <0.1 | 2.7 | <0.1 | 0.14 | 0.16 | — | 0.16 |
| 4ac | 0.19 | 2.3 | 2.4 | 0.18 | 2.0 | — | <0.1 | 2.5 | 2.3 | 2.3 | 2.0 |
| 4ad | — | — | 2.7 | — | — | — | — | — | — | — | — |
| 4ae | — | 2.9 | — | — | — | — | — | — | — | — | — |
| ADR | 0.11 | 0.13 | 0.13 | <0.1 | <0.1 | <0.1 | <0.1 | 0.15 | 0.16 | 0.16 | <0.1 |

ADR = adriamycin is the control drug

The above unexpected and excellent results demonstrate that the derivatives of compound of Formula A has higher in vitro anticancer activity, compare to the control drug.

In conclusion, the main advantages of the present inventions are that these new 4-Aza-2,3-didehydropodophyllotoxin compounds have exhibited promising in vitro cytotoxic activity. Further, these compounds have been prepared with substituted aromatic aldehydes, substituted heteroaromatic amines and tetronic acid refluxing in ethanol solvent for 1 hrs, to provides the new 4-Aza-2,3-didehydropodophyllotoxin compounds in very good yields.

We claim:
1. 4-Aza-2,3-didehydropodophyllotoxin compound of formula A

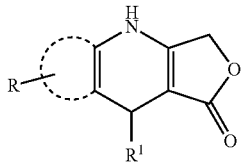

Formula A

Wherein, R is selected from 2,4 dimethoxy 5-pyrimidyl, 3-(4-methoxyphenyl) 5-isoxazolyl, 3-(4-chlorophenyl) 5-isoxazolyl, and $R^1$ is selected from 3,4,5-trimethoxyphenyl, 4-hydroxy-3-methoxyphenyl, 3-hydroxy-4-methoxyphenyl, 4-fluoro-3-methoxyphenyl.

2. The compound as claimed in claim 1, are selected from;
2,4-dimethoxy-5-(3,4,5-trimethoxyphenyl)-5,6,8,9-tetrahydrofuro[3',4':5,6]pyrido[2,3-d]pyrimidin-6-one (4a);
5-(4-hydroxy-3-methoxyphenyl)-2,4-dimethoxy-5,6,8,9-tetrahydrofuro[3',4':5,6]pyrido[2,3-d]pyrimidin-6-one (4b);
5-(3-hydroxy-4-methoxyphenyl)-2,4-dimethoxy-5,6,8,9-tetrahydrofuro[3',4:5,6]pyrido[2,3-d]pyrimidin-6-one (4c);
5-(4-fluoro-3-methoxyphenyl)-2,4-dimethoxy-5,6,8,9-tetrahydrofuro[3',4':5,6]pyrido[2,3-d]pyrimidin-6-one (4d);
3-(4-methoxyphenyl)-4-(3,4,5-trimethoxyphenyl)-4,5,7,8 tetrahydrofuro[3',4':5,6]pyrido[3,2-d]isoxazol-5-one (4aa);
4-(3-hydroxy-4-methoxyphenyl)-3-(4-methoxyphenyl)-4,5,7,8-tetrahydrofuro[3',4':5,6]pyrido[3,2-d]isoxazol-5-one (4ab);
3-(4-chlorophenyl)-4-(3,4,5-trimethoxyphenyl)-4,5,7,8-tetrahydrofuro[3',':5,6]pyrido[3,2-d]isoxazol-5-one (4ae);
3-(4-chlorophenyl)-4-(3-hydroxy-4-methoxyphenyl)-4,5,7,8-tetrahydrofuro[3',':5,6]pyrido[3,2-d]isoxazol-5-one (4ad).

3. The compound as claimed in claim 2, wherein the structural formulas of the compounds are;

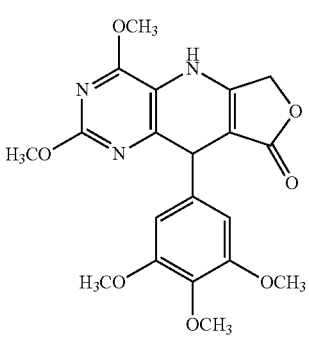

4a

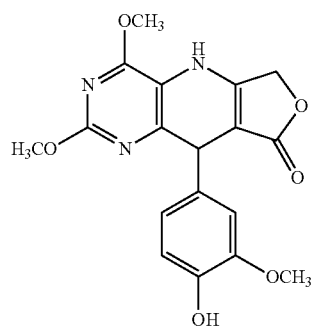

4b

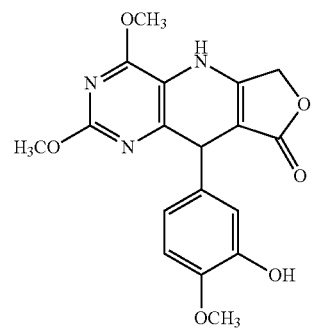

4c

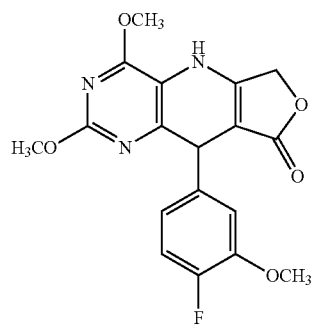

4d

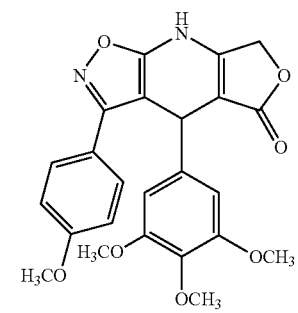

4aa

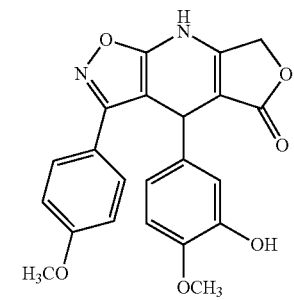

4ab

-continued

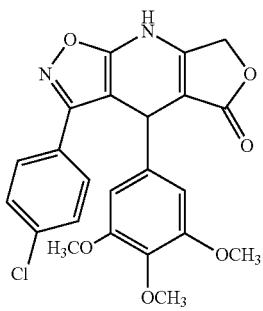
4ac

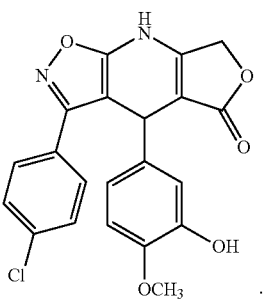
4ad

4. The compound as claimed in claim 1, wherein said compounds exhibit in vitro anticancer activity against human cancer cell lines selected from the group consisting of colon (Colo205), lung (Hop-62, A549), cervix (SiHa), prostate (PC3), oral (KB, DWD, Gurav), Ovarian (A-2780) and breast (MCF7, Zr-75-1).

5. The compounds as claimed in claim 2, wherein the concentration of the compound used for in vitro activity against breast cancer cell lines for $GI_{50}$ is in the range of 0.1 to 2.9 μm at an exposure period of at least 48 hrs.

6. The compounds as claimed in claim 2, wherein the concentration of the compound used for in vitro activity against oral cancer cell lines for $GI_{50}$ is in the range of 0.12 to 2.9 μm at an exposure period of at least 48 hrs.

7. The compounds as claimed in claim 2, wherein the concentration of the compound used for in vitro activity against colon cancer cell lines for $GI_{50}$ is in the range of 0.15 to 2.7 μm at an exposure period of at least 48 hrs.

8. The compounds as claimed in claim 2, wherein the concentration of the compound used for in vitro activity against lung cancer cell lines for $GI_{50}$ is in the range of 0.1 to 2.8 μm at an exposure period of at least 48 hrs.

9. The compounds as claimed in claim 2, wherein the concentration of the compound used for in vitro activity against prostate cancer cell lines for $GI_{50}$ is in the range of 0.16 to 2.4 μm at an exposure period of at least 48 hrs.

10. The compounds as claimed in claim 2, wherein the concentration of the compound used for in vitro activity against cervix cancer cell lines for $GI_{50}$ is in the range of 0.18 to 2.6 μm at an exposure period of at least 48 hrs.

11. The compounds as claimed in claim 2, wherein the concentration of the compound used for in vitro activity against ovarian cancer cell lines for $GI_{50}$ is in the range of 0.12 to 2.7 μm at an exposure period of at least 48 hrs.

12. A pharmaceutical composition comprising a compound of formula A as claimed in claim 1 and pharmaceutically acceptable salts, excipients and carriers thereof.

13. A process for the preparation of compound of formula A, as claimed in claim 1, comprising;
   a. refluxing substituted heteroaromatic amines, tetronic acid, and a corresponding substituted aromatic aldehydes in an organic solvent at temperature in the range of 70-78° C. for a period in the range of 60-90 min;
   b. cooling the reaction mixture as obtained in step (a) at temperature in the range of 25-35° C.;
   c. filtering the reaction mixture as obtained in step (b) at vacuum to obtain crude product followed by washing the crude product with an organic solvent;
   d. recrystallizing the crude as obtained in step (c) in an organic solvent to obtain pure 4-Aza-2,3-didehydro-podophyllotoxin compounds of formula A.

14. A process as claimed in claim 13, wherein mol ratio of heteroaromatic amines, tetronic acid, and aromatic aldehydes used is 1:1:1.

15. A process as claimed in claim 13, wherein an organic solvent is selected from the group of methanol, ethanol and DMF.

* * * * *